(12) United States Patent
Young (10) Patent No.: US 11,260,191 B2
(45) Date of Patent: Mar. 1, 2022

(54) FIXATION APPARATUS

(71) Applicant: Indian Ocean Medical Inc., Mahe (SC)

(72) Inventor: Peter Young, King's Lynn (GB)

(73) Assignee: Indian Ocean Medical Inc., Mahe (SC)

( * ) Notice: Subject to any disclaimer, the term of this patent is extended or adjusted under 35 U.S.C. 154(b) by 627 days.

(21) Appl. No.: 15/127,442

(22) PCT Filed: Mar. 20, 2015

(86) PCT No.: PCT/GB2015/050841
§ 371 (c)(1),
(2) Date: Sep. 20, 2016

(87) PCT Pub. No.: WO2015/140576
PCT Pub. Date: Sep. 24, 2015

(65) Prior Publication Data
US 2017/0119985 A1    May 4, 2017

(30) Foreign Application Priority Data

Mar. 21, 2014  (GB) ..................................... 1405132

(51) Int. Cl.
*A61M 16/04* (2006.01)
*A61M 16/08* (2006.01)
*A61M 11/00* (2006.01)

(52) U.S. Cl.
CPC ........ *A61M 16/0497* (2013.01); *A61M 11/00* (2013.01); *A61M 16/0463* (2013.01);
(Continued)

(58) Field of Classification Search
CPC .......... A61M 16/0497; A61M 16/0463; A61M 16/0465; A61M 16/08; A61M 16/0816;
(Continued)

(56) References Cited

U.S. PATENT DOCUMENTS

| 1,823,061 | A | * | 9/1931 | Pearson ................. F16L 19/08 |
| | | | | 277/607 |
| 3,734,547 | A | * | 5/1973 | Kojima ................. F16L 19/086 |
| | | | | 285/357 |

(Continued)

FOREIGN PATENT DOCUMENTS

| CN | 2344635 Y | 10/1999 |
| CN | 101801653 A | 8/2010 |

(Continued)

OTHER PUBLICATIONS

English translation of Notice of Reasons for Rejection dated Nov. 12, 2018 for Japanese Patent Application No. 2016-547872, 6 pp.
(Continued)

*Primary Examiner* — Joseph D. Boecker
*Assistant Examiner* — Brian T Khong
(74) *Attorney, Agent, or Firm* — Morgan, Lewis & Bockius LLP (57) ABSTRACT

Fixation apparatus for releasably securing a fixation structure to an airway tube of an artificial airway device is provided, the apparatus (1) being adapted to allow captive axial movement thereof relative to the airway tube (3) in a release position, and to substantially prevent axial movement thereof relative to the airway tube (3) in a secured position.

21 Claims, 6 Drawing Sheets

(52) U.S. Cl.
CPC ........ *A61M 16/0465* (2013.01); *A61M 16/08* (2013.01); *A61M 16/0816* (2013.01)

(58) Field of Classification Search
CPC .......... A61M 16/0833; A61M 16/0875; A61M 16/0493; A61M 16/0488; A61M 39/10; A61M 39/1011; Y10S 128/912; F16L 47/04; F16L 19/041; F16L 19/08; F16L 19/063; F16L 19/065; F16L 19/12; F16L 19/086; F16L 37/0925; F16L 37/138; F16L 23/04; F16L 33/224; F16L 33/035; Y10T 279/1004; Y10T 403/7054; Y10T 403/7056; Y10T 403/7058; Y10T 403/7067; B23B 31/201; B29C 48/13
See application file for complete search history.

(56) References Cited

U.S. PATENT DOCUMENTS

| | | | | |
|---|---|---|---|---|
| 3,980,325 | A * | 9/1976 | Robertson | F16L 19/08 285/249 |
| 4,226,446 | A * | 10/1980 | Burrington | F16L 33/2076 285/256 |
| 4,235,229 | A * | 11/1980 | Ranford | A61M 16/0465 128/207.17 |
| 4,270,778 | A | 6/1981 | Brownell | |
| 5,020,534 | A | 6/1991 | Pell et al. | |
| 5,072,072 | A * | 12/1991 | Bawa | H02G 3/0691 174/655 |
| 5,080,406 | A * | 1/1992 | Hyatt | B21D 39/04 285/330 |
| 5,251,616 | A | 10/1993 | Desch | |
| 5,251,617 | A | 10/1993 | Linder | |
| 5,382,059 | A * | 1/1995 | Wilson | F16L 33/2073 285/256 |
| 5,398,679 | A * | 3/1995 | Freed | A61M 16/0488 128/207.17 |
| 6,350,955 | B1 * | 2/2002 | Daoud | H02G 3/065 174/651 |
| 6,609,520 | B1 | 8/2003 | Carlsen et al. | |
| 6,851,728 | B2 * | 2/2005 | Minami | F16L 19/086 285/113 |
| 7,011,344 | B1 * | 3/2006 | Bakke | E21B 17/04 285/374 |
| 8,393,919 | B2 * | 3/2013 | Islam | H01R 9/0521 439/584 |
| 8,499,763 | B2 * | 8/2013 | Ledwith | A61M 16/0434 128/207.18 |
| 9,127,785 | B2 * | 9/2015 | Charcenko | H02G 3/22 |
| 2004/0069307 | A1 | 4/2004 | Rich et al. | |
| 2005/0084327 | A1 * | 4/2005 | Chelchowski | F16L 19/086 403/345 |
| 2008/0136175 | A1 * | 6/2008 | Hansen | F16L 19/065 285/245 |
| 2008/0202529 | A1 * | 8/2008 | Flory | A61M 16/0488 128/207.17 |
| 2008/0210232 | A1 * | 9/2008 | Trodler | A61M 16/0488 128/200.26 |
| 2009/0127803 | A1 * | 5/2009 | Chelchowski | F16L 19/065 277/622 |
| 2009/0255538 | A1 * | 10/2009 | Thomson | A61M 16/0488 128/207.17 |
| 2009/0308397 | A1 * | 12/2009 | Neame | A61M 16/0488 128/207.17 |
| 2010/0190377 | A1 * | 7/2010 | Islam | H01R 9/0527 439/584 |
| 2011/0023875 | A1 * | 2/2011 | Ledwith | A61M 16/04 128/203.12 |
| 2011/0214670 | A1 * | 9/2011 | Kost | A61M 16/00 128/200.26 |
| 2012/0216803 | A1 * | 8/2012 | Trodler | A61M 16/0497 128/200.26 |
| 2012/0227746 | A1 * | 9/2012 | Harrington | A61M 16/04 128/207.14 |
| 2014/0252760 | A1 * | 9/2014 | Paul | F16L 33/224 285/256 |

FOREIGN PATENT DOCUMENTS

| | | | | |
|---|---|---|---|---|
| CN | 101362001 Z | | 1/2011 | |
| EP | 1355101 A2 | | 10/2003 | |
| EP | 2873432 A1 | * | 5/2015 | ........ A61M 16/0465 |
| GB | 2324735 A | | 11/1998 | |
| JP | 3120990 U | | 4/2006 | |
| JP | 2013128671 A | | 9/2016 | |
| NZ | 523704 A | | 9/2004 | |
| WO | 03/061747 A1 | | 7/2003 | |
| WO | 2005/118039 A1 | | 12/2005 | |

OTHER PUBLICATIONS

English translation of First Office Action for Chinese Patent Application No. 201580009122, 5 pp.
International Search Report dated Jul. 28, 2015 for International Patent Application No. PCT/GB2015/050841.
Written Opinion of the International Searching Authority dated Jul. 28, 2015 for International Patent Application No. PCT/GB2015/050841.
Chinese Office Action dated Sep. 24, 2019 for Chinese Patent Application No. 201580009122.X, 11 pages.
European Examination Report dated Jul. 2, 2020 for European Patent Application No. 15718074.6, 5 pages.

* cited by examiner

SECTION A-A

Fig. 7

SECTION A-A

SECTION A-A

SECTION B-B

SECTION A-A
SCALE 1:1

Fig. 14

FIXATION APPARATUS

CROSS-REFERENCE TO RELATED APPLICATIONS

This application is a U.S. National Stage of International Patent Application No. PCT/GB2015/050841, filed Mar. 20, 2015, which claims the benefit of United Kingdom Patent Application No. GB 1405132.0, filed Mar. 21, 2014, each of which is incorporated by reference herein in its entirety.

The invention relates to fixation apparatus for an artificial airway device, an artificial airway device including such apparatus, an endotracheal or tracheostomy tube including said apparatus, and a method for using a said device.

Patients kept alive by mechanical ventilators or respirators often require an artificial airway such as an endotracheal, or tracheostomy tube. Such devices are very well known and have been used for many years. Over that period the art has advanced and developed to offer clinicians a wide range of devices with enhanced features and properties, sometimes at the expense of the basic requirements of ease of insertion and reliability in use. Thus when correctly placed the tube passes from outside of the mouth, through the oral cavity, through the pharyngeal space, past the vocal cords, through the laryngeal space and into the trachea. This pathway follows a variable distance and number and pattern of curves depending on the nature of the patient's anatomy and as a result correct insertion can be difficult and is a job for a skilled practitioner. Once correctly inserted, it is clearly of high importance that the tube remains so, but with patient movement such as intra-oral movements of the tongue and manipulation by medical staff the tube can move and the distal tip can pull back from the trachea and even be completely removed thereby losing control of ventilation of the lungs, which is a clinical emergency. To avoid this a number of techniques have evolved, such as at its simplest, securing the protruding portion of the tube to the patient with tape, but this does not provide for a very secure attachment. More usefully, fixation devices have been devised that can be secured to the tube and which include ancillary structures such as for example straps which allow for a more secure and convenient attachment to the patient. An example of such a device can be found in Applicant's own "Young LoTrach ETT" and "PneuX" devices.

Endotracheal and tracheostomy tubes include inflation lumens within their walls, and sometimes also include add on features, such as additional lumens for suction or irrigation. Examples of some known devices can be found in GB 2 324 735A, WO 03/061747 and WO 2005/118039, which describes devices including various configurations of lumens located within the tube wall. It has been found that problems can arise when these types of more secure fixation device are employed on tubes including lumens located within the tube wall. It will be understood that in order to function correctly, a fixation device for securing a tube to a patient must itself be secured to the tube, and, depending on its configuration, will almost certainly need to be movably fixable thereon, so that differing patient anatomies can be accommodated. A fixation device must substantially avoid placing the tube wall under compression such that wall located lumens are occluded. It is an object of the invention to seek to mitigate problems such as this.

According to a first aspect of the invention there is provided fixation apparatus for releasably securing a fixation structure to an airway tube of an artificial airway device, the apparatus being adapted to allow captive axial movement thereof relative to the airway tube in a release position, and to substantially prevent axial movement thereof relative to the airway tube in a secured position, wherein the assembly includes compression means for application of compressive load to an area of the airway tube outer surface when the apparatus is in the secured position, there being radial load focusing means disposed to focus the compressive load onto the airway tube outer surface. The invention thus provides a releasable fixation assembly that provides for secure fixation against axial movement.

It is preferred that the apparatus comprises a collet defining a bore, and that the compression means comprises resilient arms of the collet arranged to cooperate with a nut such that fitment of the arms into a bore of the nut causes progressive radial compression thereof thereby reducing the diameter of the collet bore to the secured position. It is further preferred that the internal surface of the nut and the external surfaces of the arms are provided with cooperating screw threads.

It is preferred that the radial load focusing means comprises one or more set of a plurality of closely spaced ridges. It is further preferred that the radial load focusing means comprises at least two sets of a plurality of closely spaced ridges, the sets being spaced apart from one another in the axial direction by a distance greater than the spaces between ridges in a set.

It is preferred that the fixation apparatus includes one or more fixation strap.

According to a second aspect of the invention there is provided an artificial airway device, comprising fixation apparatus as set out above. It is preferred that the artificial airway device is an endotracheal tube, and that the endotracheal tube includes at least one intra-wall lumen.

According to a third aspect of the invention there is provided a method of intubating a patient comprising the steps of inserting an endotracheal tube to a desired position and using fixation apparatus as defined above to secure the tube in the desired position.

The invention will further be described by way of example, with reference to the accompanying drawings, in which.

Referring generally to the drawings, there is illustrated fixation apparatus 1 for releasably securing a fixation structure 2 to an airway tube 3 of an artificial airway device 4, the assembly 1 being adapted to allow captive axial movement thereof relative to the airway tube 3 in a release position, and to substantially prevent axial movement thereof relative to the airway tube 3 in a secured position, wherein the apparatus includes compression means 5 for application of compressive load to an area of the airway tube outer surface when the apparatus is in the secured position, there being radial load focusing means 6 disposed to focus the compressive load onto the airway tube outer surface.

Referring firstly to FIGS. 1 and 2, and 4 to 12, in this embodiment of the invention, apparatus 1 takes the form of a fixation assembly comprising three main 30 components; a collet 7; a collet nut 8; and a fixation strap 9.

Figures 13, 14:
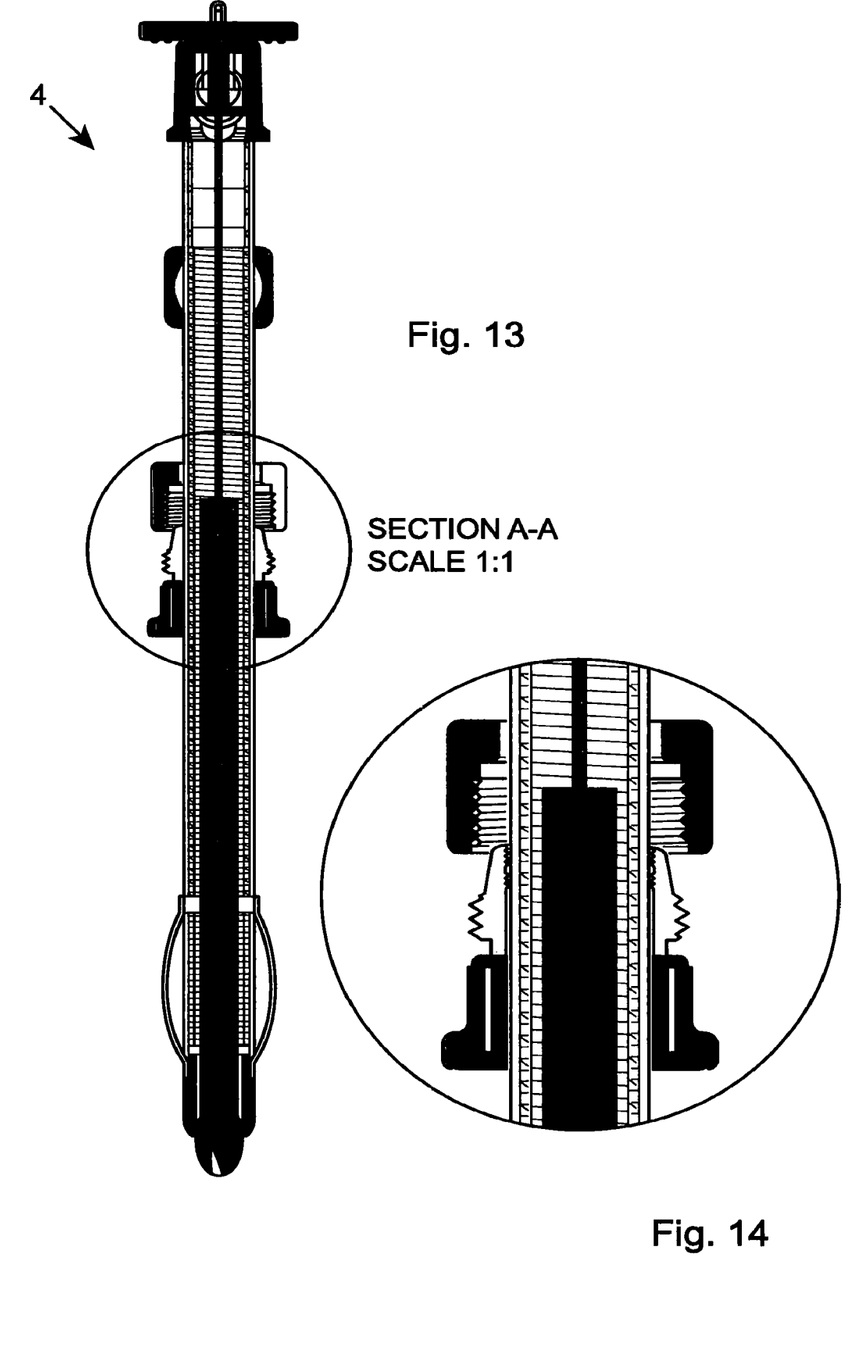
FIG. 13 is a longitudinal sectional view of an alternative device according to the invention.
FIG. 14 is an enlarged view of a section of the device of FIG. 14 showing apparatus according to the invention.

The collet 7 has a cylindrical body 10 including a through bore 11 defining a longitudinal axis and sized to receive an airway tube 3 of an artificial airway device 4 such as an endotracheal tube (FIG. 3) or a tracheostomy tube (FIG. 13). At one end the body 10 includes a circumferential end flange 12 which extends a short distance normal to the longitudinal axis of the bore. At its other end the collet 7 includes compression means 5, which here take the form of four circumferentially extending equally spaced compression arms.

Each compression arm 5 consists of an arcuate generally rectangular main body having an inner surface 14 and an outer surface 15 relative to the bore 11. On the inner surface of each arm 5 there is provided radial load focusing means 6, which here takes the form of two sets of ridges 16, each set including three individual parallel ridges, the sets being spaced apart along the longitudinal axis on the inner surface 14. On the outer surface of each arm 5 there is provided a part-screw thread 17 positioned proximal to the collet body and a cam surface 20 positioned distal thereto. At the point of attachment 18 of each arm 5 to the collet body, the thickness of the arm body is reduced, relative to the thickness of the arm body elsewhere along its length. The collet 7 is formed, for example by moulding, from a resiliently deformable plastics material and by virtue of this, and also the reduced thickness areas 18, the compression arms 5 can be moved radially inwardly as by bending, relative to the bore 11, the movement being accommodated and facilitated by gaps 19 between the arms 5.

Figure 7:
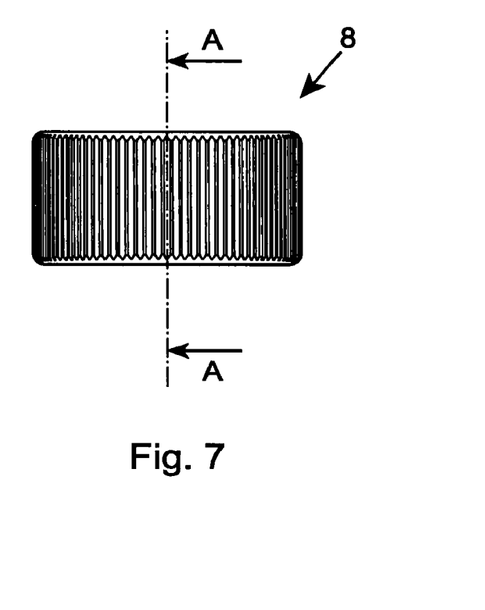
FIG. 7 is a plan view of a component of the device of FIG. 1.
Figure 8:
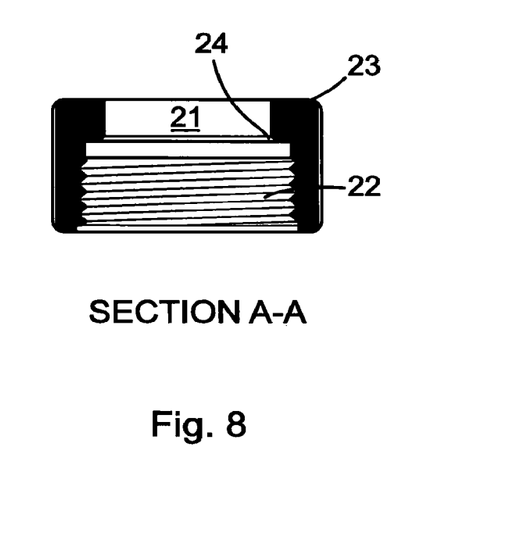
FIG. 8 is a longitudinal sectional view along line A-A in FIG. 7.
Figure 9:
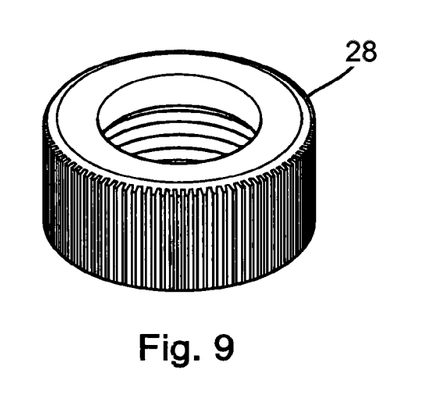
FIG. 9 is a perspective view of the component of FIG. 7.

Referring now in particular to FIGS. 7 to 9, there is illustrated collet nut 8. Collet nut 8 comprises a cylindrical body 28 including a through bore 21 dimensioned to fit onto airway tube 3 and over compression arms 5. The inner surface of bore 21 is provided with screw thread 22 and internal circumferential flange 23. Flange 23 includes bevelled edge 24 immediately adjacent to and downstream from screw thread 22. Collet nut 8 preferably is formed from a plastics material by moulding.

Figure 10:
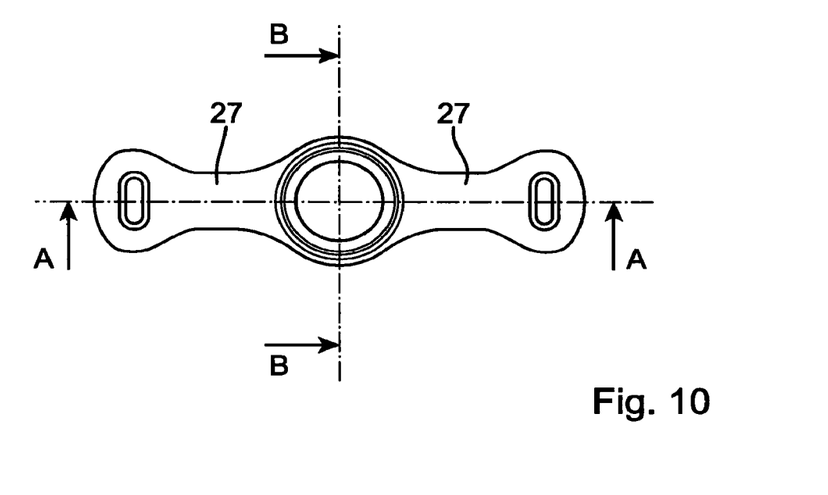
FIG. 10 is a plan view of a component of the apparatus of FIG. 1.
Figure 11:
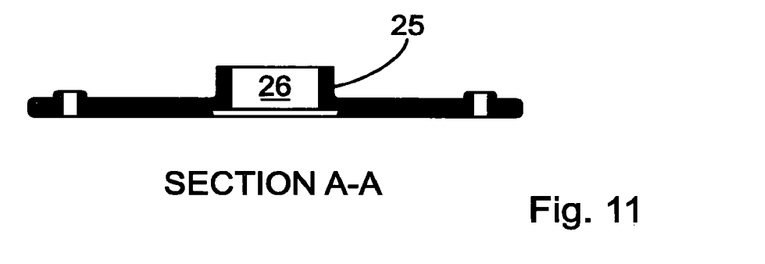
FIG. 11 is a sectional view along line A-A in FIG. 10.
Figure 12:
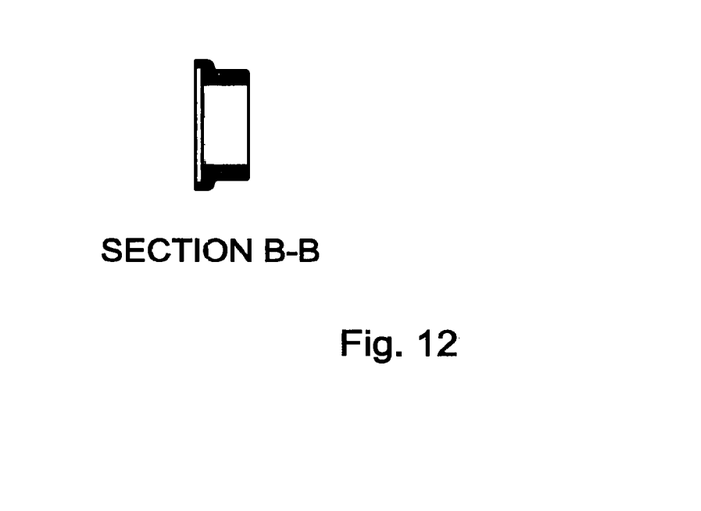
FIG. 12 is a sectional view along line B-B in FIG. 10.

Referring now in particular to FIGS. 10 to 12, there is illustrated fixation strap 9. Fixation strap 9 is of generally known type, and includes a cylindrical body 25 dimensioned to fit onto an airway tube 3 via through-bore 26, and radially outwardly projecting wings 27. It is preferred that collet strap 9 comprises a resilient material such as silicone.

Figure 1:
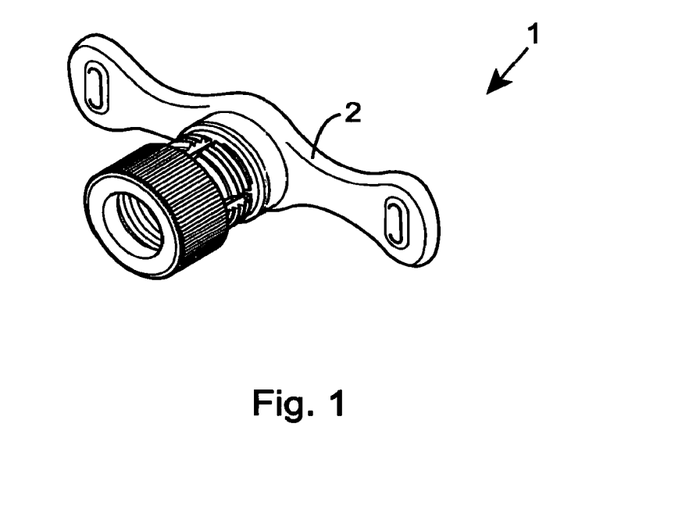
FIG. 1 is a perspective view of apparatus according to the invention.
Figure 2:
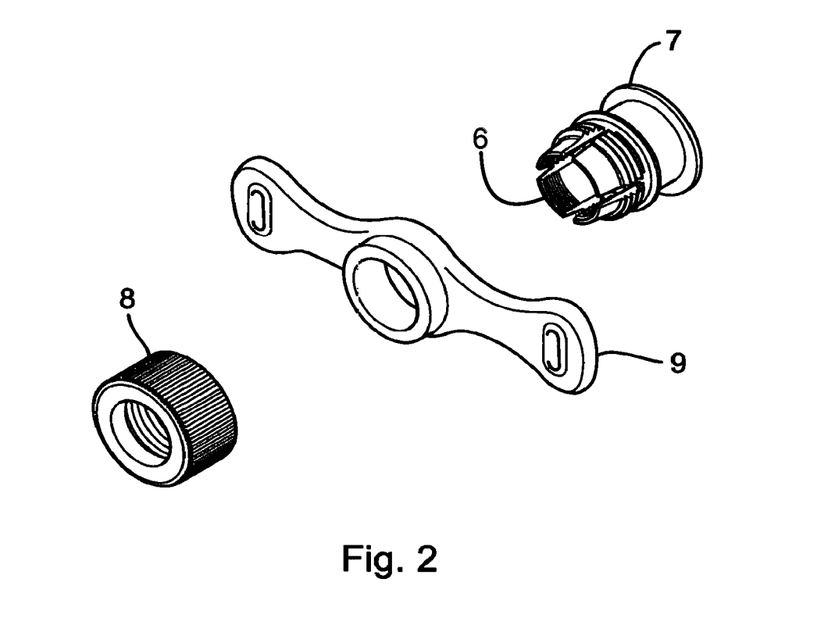
FIG. 2 is an exploded view of the apparatus of FIG. 1.
Figure 3:
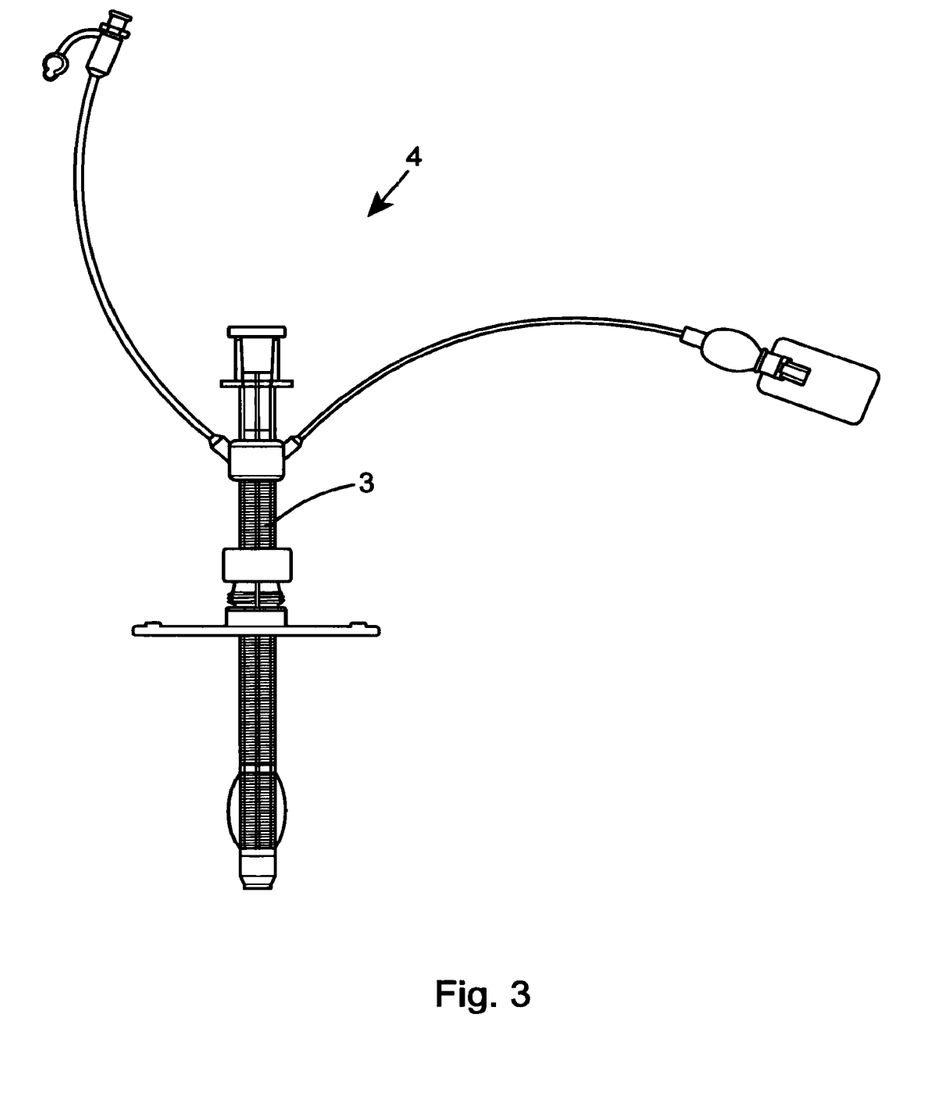
FIG. 3 is a front view of an airway device according to the invention.
Figure 4:
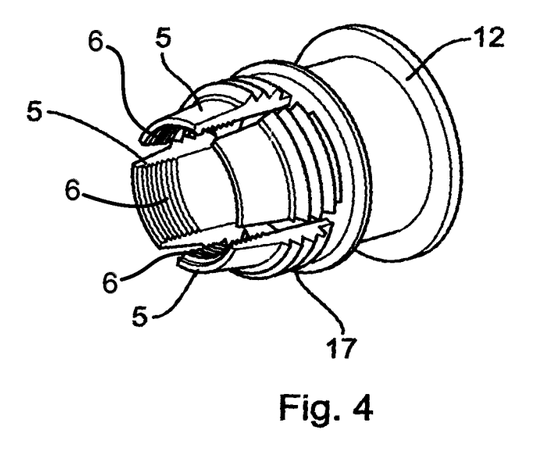
FIG. 4 is an enlarged perspective view of a component of the apparatus of FIG. 1.
Figure 5:
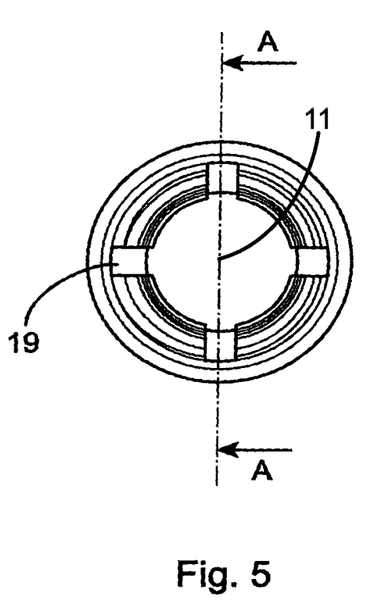
FIG. 5 is an end view of the component of FIG. 4.
Figure 6:
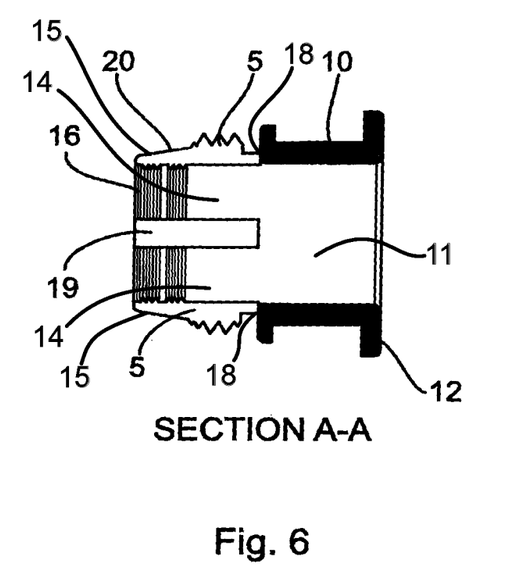
FIG. 6 is a longitudinal sectional view along line A-A in FIG. 5.

FIGS. 3 and 13 illustrate how apparatus 1 is used in conjunction with, respectively, an endotracheal tube and a tracheostomy tube. In use, the components of apparatus 1 are placed onto the airway tube 3 of a device 4 by sliding, such that the collet 7 is disposed with collet arms 5 directed towards the proximal end, and in loose engagement with nut 8. It is important that nut 8 is oriented with screw thread 22 towards arms 5. Fixation strap 9 is conveniently mated to collet 7 prior to placement onto the tube. The collet 7 and strap 9 are thus captive on and freely slidable axially along the tube 3 to any desired position. Once a desired position has been selected, an operator can manipulate nut 8 axially so that collet arms 5 are received within bore 21 and screw threads 17 and 22 engage. Rotation of nut 8 relative to collet 7 about the threads 17 brings the two parts axially together and causes cam surfaces 20 of arms 5 to contact bevelled edge 24. As the collet 7 and nut 8 move closer together, edge 24 slides over cam surfaces 20, causing arms 5 to move radially inwardly, reducing the diameter of the gaps 19 therebetween and accordingly the bore defined by the collet 7 and arms 5 are thus brought into contact with the surface of the airway tube 3 via ridges 16.

Ridges 16 achieve an important dual function, which is to both form a secure but releasable connection between collet 7 and airway tube 3, whilst also spreading the radial compression sufficiently around the outer surface of the airway tube 3 to avoid crushing its surface and occluding sub-surface structures such as lumens that are often formed within the wall. It has been found that this dual function is most effectively achieved by the provision of a group or groups of ridges 16 as described above, rather than a single ridge. A single ridge can focus compression onto too small an area of the surface if the nut 8 is over-tightened. In clinical situations, particularly emergency situations, staff cannot and should not be expected to make precise adjustments to apparatus of this kind because they are required to focus their attention on the welfare of the patient. The invention thus provides a type of safety check that helps ensure that a secure fixation is achieved without damage to delicate tube structures and without the need for precise operation in the clinical setting.

The invention claimed is:

1. A fixation apparatus for releasably securing a fixation structure to an airway tube of an artificial airway device, comprising:
   the fixation apparatus being adapted to allow captive axial movement thereof along an outer surface of the airway tube in a release position, and to prevent axial movement thereof relative to the airway tube in a secured position such that the fixation apparatus can be positioned at any point along a longitudinal axis of the airway tube; and
   a collet defining a bore and a collet nut, the collet comprising a cylindrical body and a substantially constant internal diameter extending an entire length of the collet, the substantially constant internal diameter being sized to receive the airway tube having a substantially constant external diameter,
   wherein the fixation apparatus includes compression means for application of compressive load to an area of the airway tube outer surface when the fixation apparatus is in the secured position, there being radial load focusing means disposed to focus the compressive load onto the airway tube outer surface,
   wherein the compression means comprises resilient arms of the collet arranged to cooperate with the collet nut such that fitment of the resilient arms into the bore of the collet nut by rotation causes progressive radial compression thereof thereby reducing a diameter of the collet bore to the secured position,
   wherein the radial load focusing means comprises at least two sets of a plurality of closely spaced ridges on each of the resilient arms,
   wherein the at least two sets of the plurality of closely spaced ridges are axially spaced apart from one another along the longitudinal axis of the airway tube by a distance greater than a distance between individual ridges in a set, and wherein the at least two sets of the plurality of closely spaced ridges are axially spaced apart on the longitudinal axis from one another by a band, the band being free of ridges.

2. The fixation apparatus according to claim 1, wherein an internal surface of the collet nut and external surfaces of the resilient arms comprise cooperating screw threads.

3. The fixation apparatus according to claim 1 further comprising:
one or more fixation straps.

4. The fixation apparatus according to claim 1, wherein the band is parallel to the closely spaced ridges.

5. The fixation apparatus according to claim 1, wherein the band extends circumferentially on an inner surface of the fixation apparatus from a first axially extending gap to a second axially extending gap.

6. The fixation apparatus according to claim 1, wherein the collet includes at most four slits.

7. The fixation apparatus according to claim 1, wherein the collet includes one or more slits extending less than a majority of the entire length of the collet.

8. The fixation apparatus according to claim 1, wherein the collet includes an outer surface having a threaded portion disposed on one or more of the resilient arms.

9. The fixation apparatus according to claim 1, wherein the collet includes a distal end and a proximal end, the distal end including the compression means and the at least two sets of the plurality of closely spaced ridges, and the proximal end including a flange.

10. The fixation apparatus according to claim 9, wherein the distal end of the collet includes a tapered outer surface.

11. The fixation apparatus according to claim 9, wherein the at least two sets of the plurality of closely spaced ridges are disposed along an inner surface of the distal end.

12. The fixation apparatus according to claim 9, wherein collet includes an outer surface having a threaded portion, the threaded portion disposed between the at least two sets of the plurality of closely spaced ridges and the proximal end.

13. An artificial airway device for use in establishing an airway in a patient, the artificial airway device comprising:
an airway tube;
a fixation apparatus for releasably securing a fixation structure to the airway tube, the fixation apparatus being adapted to allow captive axial movement thereof along an outer surface of the airway tube in a release position, and to prevent axial movement thereof relative to the airway tube in a secured position such that the fixation apparatus can be positioned at any point along a longitudinal axis of the airway tube; and
a collet defining a bore and a collet nut, the collet comprising a cylindrical body and a substantially constant internal diameter extending an entire length of the collet, the substantially constant internal diameter being sized to receive the airway tube having a substantially constant external diameter,
wherein the fixation apparatus includes compression means for application of compressive load to an area of the airway tube outer surface when the fixation apparatus is in the secured position, there being radial load focusing means disposed to focus the compressive load onto the airway tube outer surface,
wherein the compression means comprises resilient arms of the collet arranged to cooperate with the collet nut such that fitment of the resilient arms into the bore of the collet nut by rotation causes progressive radial compression thereof thereby reducing a diameter of the collet bore to the secured position,
wherein the radial load focusing means comprises at least two sets of a plurality of closely spaced ridges on each of the resilient arms,
wherein the at least two sets of the plurality of closely spaced ridges are axially spaced apart from one another along the longitudinal axis of the airway tube by a distance greater than a distance between individual ridges in a set, and
wherein the at least two sets of the plurality of closely spaced ridges are axially spaced apart on the longitudinal axis from one another by a band, the band being free of ridges.

14. The artificial airway device according to claim 13, wherein the airway tube comprises an endotracheal tube.

15. The artificial airway device according to claim 13, wherein the airway tube comprises a tracheostomy tube.

16. The artificial airway device according to claim 13, wherein the airway tube includes an intra-wall lumen.

17. A method of intubating a patient comprising the steps of inserting the artificial airway device according to claim 13 to a desired position and securing it in place, wherein the airway tube comprises an endotracheal tube.

18. A method of intubating a patient comprising the steps of inserting the artificial airway device according to claim 13 to a desired position and securing it in place, wherein the airway tube comprises a tracheostomy tube.

19. A fixation apparatus for releasably securing a fixation structure to an airway tube, the fixation apparatus comprising:
a collet defining a bore and a collet nut, the collet comprising a cylindrical body and a substantially constant internal diameter extending an entire length of the collet and configured to allow the collet to be positioned at any location along a longitudinal axis of the airway tube, the collet including one or more slits extending along less than a majority of the entire length of the collet, the collet comprising a plurality of resilient arms separated from each other by the one or more slits, wherein each of the plurality of resilient arms includes a tapered outer surface and a threaded portion disposed on the tapered outer surface, and at least two sets of a plurality of closely spaced ridges on each one of the plurality of resilient arms;
a collet nut threadedly coupled to the collet and extending at least partially over the resilient arms,
wherein the at least two sets of the plurality of closely spaced ridges are axially spaced apart from one another along a longitudinal axis of the body by a distance greater than a distance between individual ridges in a set, and
wherein the at least two sets of the plurality of closely spaced ridges are axially spaced apart on the longitudinal axis from one another by a band, the band being free of ridges, and the at least two sets of the plurality of closely spaced ridges being disposed along an inner surface of the plurality of the resilient arms.

20. The fixation apparatus according to claim 19 further comprising:
the fixation structure having a pair of diametrically opposed and radially outwardly extending projection wings, each of the diametrically opposed and radially outwardly extending projection wings including a bulbous end having an aperture, wherein the collet includes a radially outwardly extending flange at a proximal end of the collet abutting the fixation structure.

21. The fixation apparatus according to claim 19, wherein the collet nut includes a proximal bore having a proximal diameter and distal bore having a distal diameter, the distal diameter being smaller than the proximal diameter to form a radially inwardly extending flange.

\* \* \* \* \*